United States Patent [19]
Papantoniou

[11] 3,946,749
[45] Mar. 30, 1976

[54] HAIR COSMETIC COMPOSITIONS BASED ON GRAFTED AND CROSSLINKED COPOLYMERS
[75] Inventor: Christos Papantoniou, Epinay-sur-Seine, France
[73] Assignee: L'Oreal, Paris, France
[22] Filed: June 19, 1973
[21] Appl. No.: 371,513

[30] Foreign Application Priority Data
June 20, 1972 Luxemburg............................ 65552

[52] U.S. Cl............. 132/7; 260/78.4 D; 260/78.4 F; 260/80.72; 260/80.76; 260/874; 424/DIG. 1; 424/DIG. 2; 424/47; 424/70; 424/71; 424/78
[51] Int. Cl.$^2$.................... A45D 7/00; A61K 7/11
[58] Field of Search............. 424/70, 71, 78, DIG. 1, 424/DIG. 2, 47; 260/80.76, 874; 132/7

[56] References Cited
UNITED STATES PATENTS

| | | | |
|---|---|---|---|
| 3,188,275 | 6/1965 | Erlemann.............................. | 424/71 |
| 3,546,321 | 12/1970 | Jabloner et al..................... | 260/874 |
| 3,579,629 | 5/1971 | Pasero et al.......................... | 424/47 |
| 3,726,288 | 4/1973 | Nowak et al....................... | 424/71 X |
| 3,776,983 | 12/1973 | Iovine et al...................... | 260/874 X |

Primary Examiner—V. D. Turner
Assistant Examiner—Vera C. Clarke
Attorney, Agent, or Firm—Mason, Mason & Albright

[57] ABSTRACT

A cosmetic composition is provided which comprises at least one graft and cross-linked copolymer obtained by copolymerization of:
 a. at least one non-ionic monomer,
 b. at least one ionic monomer or N-vinyl pyrrolidone,
 c. polyethylene glycol, and
 d. a cross-linking agent selected from ethylene glycol dimethacrylate, diallyl o-, m- and p-phthalates, a divinylbenzene, tetrallyloxyethane and a polyallylsucrose possessing 2 to 5 allyl groups per mol of sucrose, and a cosmetically acceptable vehicle.

Such compositions are particularly useful as hair lacquers and wavesetting lotions; they adhere well to the hair while giving a good glossy appearance. Certain of the copolymers are novel.

5 Claims, No Drawings

HAIR COSMETIC COMPOSITIONS BASED ON GRAFTED AND CROSSLINKED COPOLYMERS

The present invention relates to new cosmetic compositions based on grafted and crosslinked copolymers and to certain new copolymers used therein.

It has already been proposed to use in cosmetic compositions such as lacquers and wavesetting lotions various different types of homo- and co-polymers. Among these, one can mention polyvinyl pyrrolidone, copolymers such as the vinylpyrrolidone/vinyl acetate copolymer; copolymers of vinyl acetate and an unsaturated carboxylic acid such as crotonic acid; copolymers resulting from the polymerization of vinyl acetate, crotonic acid and an acrylic or methacrylic ester or an alkyl vinyl ether; copolymers resulting from the copolymerization of vinyl acetate, crotonic acid and a vinyl ester of an acid with a long carbon chain or an allyl or methallyl ester of an acid with a long carbon chain; copolymers resulting from the copolymerization of an ester of an unsaturated alcohol and a saturated carboxylic acid with a short carbon chain, of an unsaturated acid with a short carbon chain, and of at least one ester of a saturated alcohol with a long carbon chain and an unsaturated acid with a short carbon chain, and copolymers resulting from the polymerization of at least one unsaturated ester and at least one unsaturated acid.

Some of these copolymers, which have been used to a very large extent, do possess good affinity for the keratin of the hair but nevertheless they do not have the combination of properties which are required for the production of excellent lacquers and wavesetting lotions.

It has now been found, very surprisingly, according to the present invention, that it is possible to produce excellent cosmetic compositions, in particular lacquers or wavesetting lotions, using a particular type of copolymer, which is, at the same time, grafted and cross-linked.

According to the present invention, there is provided a cosmetic composition containing, in a suitable cosmetic vehicle, at least one graft and cross-linked copolymer obtained by copolymerization of:
a. at least one non-ionic monomer,
b. at least one ionic monomer or N-vinylpyrrolidone,
c. polyethylene glycol, and
d. a cross-linking agent chosen from the group consisting of ethylene glycol dimethacrylate, diallyl phthalates, divinylbenzenes, tetraallyloxyethane and polyallylsucroses possessing 2 to 5 allyl groups per mol of sucrose.

Such cosmetic compositions give rise to better results than those available hitherto. Lacquers or wavesetting lotions containing such copolymers form films having a lacquerability which is noticeably better than that obtained with the known resins.

The copolymers which can be used according to the invention also impart other particularly valuable advantages to the lacquers and wavesetting lotions. In particular, the films obtained have a markedly higher gloss than that obtained with the known polymers. Furthermore, they possess a very great affinity for the hair, so that they make the hair style keep better, which enables the hair to be combed out without significant loss of the copolymer film. It is, of course, known that with the known hair lacquers and the like when one combs the hair effectively all of the resin becomes detached from the hair and falls in the form of a white powder. In contrast, with the compositions of the present invention, it is possible to comb the hair without significant loss of the copolymer although the copolymer can nevertheless easily be removed by brushing or by washing with a conventional shampoo.

By the expression "graft and crosslinked copolymer" is meant a copolymer which possesses a principal chain with branches or grafts which are attached to one another with the aid of a cross-linking agent. Thus, in effect, these grafted and cross-linked copolymers possess a network of branches the density of which depends largely on the degree of unsaturation of the cross-linking agent.

Grafted copolymers are, of course, well-known and they can be represented schematically as follows:

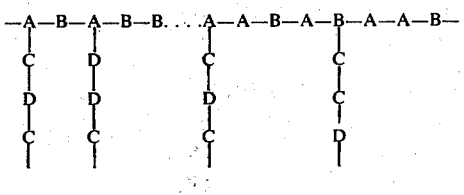

FIGURE 1

The main chain — A — B — A — B — B ... A — A — B — A — B ... forms "the backbone" of the graft copolymer and the chain links — C — D ... D — C — constitute the grafts. A graft and cross-linked copolymer can be represented schematically as follows:

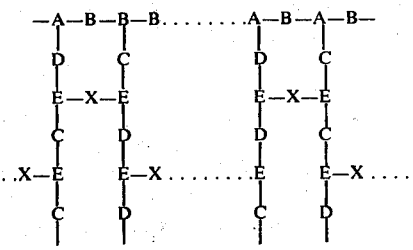

FIGURE 2

The principal chain or "backbone" — A — B — B — B ... A — B — A — B — is identical to that in the graft copolymer, as are the grafts. However, in the case of the graft and cross-linked copolymers, the chain links — E — X — E — which connect the various grafts and/or the various "backbones" of the polymers present.

These chain links E — X — E originate from the cross-linking agent which, if it is doubly unsaturated (as in FIG. 2), gives rise to two-dimensional cross-linked networks. As indicated above, however, the cross-linking agent can have a higher degree of unsaturation which gives rise to three-dimensional structures. The degree of unsaturation is at least 2 and can, in the case of the polyallylsucroses, be 5.

Typical non-ionic monomers which can be used include: vinyl acetate, vinyl stearate, vinyl laurate, vinyl propionate, allyl stearate, allyl laurate, diethyl maleate, allyl acetate, methyl methacrylate, cetyl vinyl ether, stearyl vinyl ether and hexene-1.

Similarly, the ionic monomers can also be of very varied type; typical examples include monomers containing acid groups such as crotonic acid, allyloxyacetic acid, vinylacetic acid, maleic acid, acrylic acid and methacrylic acid.

The prepolymer onto which the grafting takes place suitably has a molecular weight between 200 and several millions, preferably between 300 and 30,000.

The graft and cross-linked copolymers used in the present invention are preferably derived from:

a. 5 to 85% by weight of at least one nonionic monomer,
b. 3 to 80% by weight of at least one ionic monomer or N-vinylpyrrolidone,
c. 2 to 50%, preferably 5 to 30%, by weight of polyethylene glycol, and
d. 0.01% to 8% by weight based on the total weight of (a) + (b) + (c) of cross-linking agent.

Thus, if 246 g of vinyl acetate (82%), 24 g of crotonic acid (8%) and 30 g of polyethylene glycol (10%) are copolymerized, the amount of cross-linking agent can vary between 0.03 g (0.01%) and 24 g (8%).

The graft and cross-linked copolymers thus defined generally have a molecular weight of between 10,000 and 1,000,000, but preferably between 15,000 and 500,000.

The cosmetic compositions according to the invention can be either in the form of wavesetting lotions or in the form of hair lacquers.

The wavesetting lotions according to the invention are suitably in the form of aqueous or aqueous-alcoholic solutions containing from 5 to 70% by weight of alcohol, the concentration of graft and cross-linked copolymer being between 0.4 and 5% by weight. The alcohols generally used for the production of such wavesetting lotions are preferably lower aliphatic alcohols (i.e. of 1 to 6, suitably 1 to 4, carbon atoms) such as ethanol or isopropanol.

The hair lacquers according to the invention are suitably obtained by dissolving at least one graft and cross-linked copolymer, as defined above, in an alcohol, this solution being placed in an aerosol container and mixed with a liquefied propellant gas under pressure. For example, a hair lacquer according to the invention can be obtained by adding 0.5 to 4% by weight of at least one graft and cross-linked copolymer to a mixture consisting of ¼ to ⅓ of an anhydrous aliphatic alcohol such as ethanol or isopropanol and ¾ to ⅔ of a propellant or of a mixture of liquefied propellants such as a halogenated hydrocarbon, for example trichlorofluoromethane or dichlorodifluoromethane.

If the graft and cross-linked copolymers possess free carboxylic acid groups, the latter can be neutralized with a base, generally used in an amount between 50 and 100% of the amount corresponding to stoichiometric neutralization, the base employed being either an organic or inorganic base, such as ammonia, monoethanolamine, diethanolamine, triethanolamine, an isopropanolamine, morpholine, 2-amino-2-methyl-1-propanol and 2-amino-2-methyl-1,3-propanediol.

Of course, it is possible to add to the cosmetic compositions according to the invention adjuvants such as plasticizers, perfumes, dyestuffs or other adjuvants conventionally employed in hair compositions.

The present invention also provides a process for wavesetting hair which comprises impregnating the hair with a lotion according to the invention, winding up the hair on wavesetting rollers, suitably of diameter 15 to 30 mm and drying the hair thus rolled up.

The present invention also provides the graft and cross-linked copolymers obtained by the copolymerization of:

a. 5 to 85% by weight of at least one nonionic monomer which is vinyl acetate, vinyl stearate, vinyl laurate, vinyl propionate, allyl stearate, allyl laurate, diethyl maleate, allyl acetate, methyl methacrylate, cetyl vinyl ether, stearyl vinyl ether or hexene-1,
b. 3 to 80% by weight of at least one ionic monomer which is crotonic acid, allyloxyacetic acid, vinylacetic acid, maleic acid, acrylic acid or methacrylic acid, or N-vinylpyrrolidone,
c. 2 to 50% by weight, preferably 5 to 30%, by weight of polyethylene glycol and
d. 0.01 to 8% by weight based on the total weight of (a) + (b) + (c), of a cross-linking agent which is ethylene glycol dimethacrylate, diallyl phthalate, a divinylbenzene, tetraallyloxyethane or a polyallylsucrose having 2 to 5 allyl groups per mol of sucrose.

Naturally, the characteristics (molecular weight, structure and the like) indicated above for the graft and cross-linked copolymers which can be used in the cosmetic compositions according to the invention equally apply to these new copolymers.

The graft and cross-linked copolymers can be prepared by conventional polymerization methods, for example in bulk, in suspension, as an emulsion or in solution in a solvent. Preferably, the polymerization is carried out in bulk or in suspension.

Generally conventional radical polymerization initiators are used, the particular choice depending mainly on the different monomers used and on the reaction medium. Examples of such initiators which can be used include peroxides such as benzoyl peroxide, lauroyl peroxide, acetyl peroxide and benzoyl hydroperoxide; catalysts which on decomposition evolve an inert gas, such as azo-bis-isobutyronitrile; and oxidation-reduction catalysts such as sodium persulphate, sodium sulphite and hydrogen peroxide. The initiator concentration is generally between 0.2 and 15%, preferably between 0.5 and 12% by weight relative to the total weight of the reactants (monomers, polyethylene glycol and cross-linking agent).

In suspension polymerization it is important that the various reactants should not be miscible with water or with the inert liquid used for carrying out the polymerization. Hence, if water is used as the suspension medium, it is important that it should be saturated with an inorganic salt such as sodium chloride, because polyethylene glycol is soluble in water. If one of the monomers is also soluble in water (which is the case with acids), the effect of adding sodium chloride is to cause it to be suspended; hence all the reactants are present in the form of droplets.

The suspending agents which may be used according to the present invention include hydroxyethylcellulose, known under the trade name of "CELLOSIZE", cross-linked polyacrylic acid known under the name of "CARBOPOL" and the polyvinyl alcohols known under the trade name of "RHODOVIOL".

If the polymerization is carried out in an emulsion, the reaction generally takes place in the presence of an emulsifying agent such as potassium stearate, potassium palmitate, potassium laurate, or laurylamine hydrochloride.

The molecular weight of the graft and cross-linked copolymers can be regulated by introducing, during the polymerization, small amounts, for example 0.05 to 0.4% by weight, of a chain regulator such as an aldehyde, for example butyraldehyde, halogenated compounds such as chloroform, bromoform and carbon tetrachloride and mercaptans such as laurylmercaptan.

The following Examples further illustrate the present invention.

EXAMPLES OF PREPARATION OF COPOLYMERS

EXAMPLE 1

400 g of an aqueous solution containing 104 g of sodium chloride and 0.8 g of Cellosize are introduced into a 2 liter flask equipped with a mechanical stirrer, a nitrogen inlet tube, a thermometer and a condenser. A solution consisting of 246 g of vinyl acetate, 24 g of crotonic acid, 30 g of polyethylene glycol (molecular weight (MW) = 20,000), 0.6 g of tetraallyloxyethane and 6 g of 100% strength benzoyl peroxide is then introduced. After the addition, the mixture is heated with stirring, and under reflux, for about 8 hours. After this time, the polymerization is complete. The beads obtained are washed and isolated in the usual manner.

Yield: 85%
Acid number: 53.8
Viscosity ... (5% strength solution in DMF at 35°C): 7.73 cps.

EXAMPLE 2

220 g of an aqueous solution containing 77 g of sodium chloride and 0.44 g of Cellosize are introduced into a 1 liter flask equipped with a mechanical stirrer, a nitrogen inlet tube, a thermometer and a condenser. Thereafter a solution consisting of 82 g of vinyl acetate, 8 g of crotonic acid, 10 g of polyethylene glycol (molecular weight: 20,000), 15 g of diallyl ether and 10 g of azo-bis-isobutyronitrile is introduced. After the addition, the mixture is heated at 70°C for 24 hours. After this time, the polymerization is complete. The beads obtained are washed and isolated in the usual manner.

Yield: 82%

EXAMPLE 3

The following are polymerized according to the process described in Example 1:

| | |
|---|---|
| Vinyl acetate | 63 g |
| N-vinyl pyrrolidone | 27 g |
| Polyethylene glycol of MW 20,000 | 10 g |
| Tetraallyloxyethane | 0.1 g |
| Azo-bis-isobutyronitrile | 4 g |
| Sodium chloride | 152 g |
| 0.06% strength solution of Cellosize in water | 400 g |

Characteristics of the polymer obtained:
Viscosity ... (5% strength solution in DMF at 35°C): 2.71 cps

EXAMPLE 4

The following are polymerized according to the process described in Example 1:

| | |
|---|---|
| Vinyl acetate | 72 g |
| Crotonic acid | 8 g |
| Polyethylene glycol of MW 20,000 | 20 g |
| Tetraallyloxyethane | 0.2 g |
| Benzoyl peroxide | 2 g |
| 0.2% strength solution of Cellosize in water | 200 g |
| Sodium chloride | 76 g |

Characteristics of the polymer obtained:
Acid number: 57
Viscosity (5% strength solution in DMF at 35°C): 6 cps.

EXAMPLE 5

The following are polymerized according to the process described in Example 1:

| | |
|---|---|
| Vinyl acetate | 82 g |
| Crotonic acid | 8 g |
| Polyethylene glycol of MW 4,000 | 10 g |
| Tetraallyloxyethane | 0.2 g |
| 0.2% strength solution of Cellosize in water | 200 g |
| Sodium chloride | 76 g |
| Benzoyl peroxide | 2 g |

Characteristics of the polymer obtained:
Acid number: 57.8
Viscosity (5% strength solution in DMF at 35°C): 3.17 cps.

EXAMPLE 6

The following are polymerized according to the process described in Example 1:

| | |
|---|---|
| Vinyl acetate | 82 g |
| Crotonic acid | 8 g |
| Polyethylene glycol of MW 1,500 | 10 g |
| Tetraallyloxyethane | 0.2 g |
| 0.2% strength solution of Cellosize in water | 200 g |
| Sodium chloride | 76 g |
| Benzoyl peroxide | 2 g |

Characteristics of the polymer obtained:
Acid number: 57.9
Viscosity (5% strength solution in DMF at 35°C): 2.83 cps.

EXAMPLE 7

The following are polymerized according to the process described in Example 1:

| | |
|---|---|
| Vinyl acetate | 70 g |
| Crotonic acid | 20 g |
| Polyethylene glycol of MW 20,000 | 10 g |
| Tetraallyloxyethane | 0.2 g |
| Benzoyl peroxide | 2 g |
| 0.4% strength solution of Cellosize in water | 200 g |
| Sodium chloride | 76 g |

Characteristics of the polymer obtained:
Acid number: 136
Viscosity (5% strength solution in DMF at 35°C): 2.18 cps

EXAMPLE 8

The following are polymerized analogously to Example 1:

| | |
|---|---|
| Vinyl acetate | 85 g |
| Crotonic acid | 5 g |
| Polyethylene glycol of MW 40,000 | 10 g |
| Tetraallyloxyethane | 0.2 g |
| Benzoyl peroxide | 2 g |
| 0.2% strength solution of Cellosize in water | 200 g |
| Sodium chloride | 76 g |

Characteristics of the polymer obtained:

Acid number: 39
Viscosity (5% strength solution in DMF at 35°C): 5.15 cps

EXAMPLE 9

The following are polymerized analogously to Example 1:

| | |
|---|---|
| Vinyl acetate | 82 g |
| Crotonic acid | 8 g |
| Polyethylene glycol of MW 20,000 | 10 g |
| Diallyl phthalate | 0.2 g |
| Benzoyl peroxide | 10 g |
| 0.2% strength solution of Cellosize in water | 200 g |
| Sodium chloride | 76 g |

Characteristics of the polymer obtained:
Acid number: 57
Viscosity (5% strength solution in DMF at 35°C): 3.34 cps.

EXAMPLE 10

The following are polymerized analogously to Example 1:

| | |
|---|---|
| Vinyl acetate | 82 g |
| Crotonic acid | 8 g |
| Polyethylene glycol of MW 20,000 | 10 g |
| Diallylmelamine | 0.2 g |
| Azo-bis-isobutyronitrile | 2.2 g |
| 0.2% strength solution of Cellosize in water | 200 g |
| Sodium chloride | 76 g |

Characteristics of the polymer obtained:
Acid number: 59
Viscosity (5% strength solution in DMF at 35°C): 2.77 cps.

EXAMPLE 11

10 g of vinyl stearate, 10 g of allyloxyacetic acid, 0.02 g of tetraallyloxyethane, 10 g of polyethylene glycol of molecular weight 20,000 and 2 g of 100% strength benzoyl peroxide, dissolved in 70 g of vinyl acetate, are introduced into a 1 liter flask equipped with a mechanical stirrer, a nitrogen inlet tube and a condenser.

The mixture is heated under reflux, and then at 80°C for 8 hours.

A polymer (with the following properties) is obtained:
Acid number: 31.4
Viscosity (2% of polymer neutralized with 2-amino-2-methyl-1-propanol, dissolved in 50% strength aqueous ethanol, at 34.6°C): 3.5 cps.

EXAMPLE 12

The following are polymerized according to the process described in Example 11:

| | |
|---|---|
| Vinyl acetate | 71 g |
| Allyl stearate | 15 g |
| Allyloxyacetic acid | 4 g |
| Polyethylene glycol of MW 20,000 | 10 g |
| Tetraallyloxyethane | 0.2 g |
| Benzoyl peroxide | 3 g |

Characteristics of the polymer obtained:
Acid number: 25
Viscosity (2% of polymer neutralized with 2-amino-2-methyl-1-propanol, dissolved in 50% strength aqueous ethanol, at 34.6°C): 2.84 cps.

EXAMPLE 13

The following are polymerized analogously to Example 11:

| | |
|---|---|
| Vinyl acetate | 65 g |
| Allyl stearate | 10 g |
| Allyloxyacetic acid | 5 g |
| Polyethylene glycol of MW 20,000 | 20 g |
| Tetraallylsucrose | 0.2 g |
| Benzoyl peroxide | 3 g |

Characteristics of the polymer obtained:
Acid number: 23
Viscosity (2% of polymer neutralized with 2-amino-2-methyl-1-propanol, dissolved in 50% strength aqueous ethanol, at 34.6°C): 3.18 cps.

EXAMPLE 14

The following are polymerized analogously to Example 11:

| | |
|---|---|
| Vinyl acetate | 70 g |
| Allyl acetate | 10 g |
| Crotonic acid | 10 g |
| Polyethylene glycol of MW 20,000 | 10 g |
| Tetraallyloxyethane | 0.2 g |
| Benzoyl peroxide | 3 g |

Characteristics of the polymer obtained:
Acid number: 91
Viscosity (5% strength solution in DMF at 35°C): 3.73 cps.
Viscosity (2% of polymer neutralized with 2-amino-2-methyl-1-propanol, dissolved in 50% strength aqueous ethanol, at 34.6°C): 3.63 cps.

EXAMPLE 15

The following are polymerized analogously to Example 11:

| | |
|---|---|
| Vinyl acetate | 70 g |
| Methyl methacrylate | 10 g |
| Crotonic acid | 10 g |
| Polyethylene glycol of MW 20,000 | 10 g |
| Tetraallyloxyethane | 0.2 g |
| Benzoyl peroxide | 3 g |

Characteristics of the polymer obtained:
Acid number: 57
Viscosity (2% of polymer neutralized with 2-amino-2-methyl-1-propanol, dissolved in 50% strength aqueous ethanol, at 34.6°C): 5.5 cps.

EXAMPLE 16

The following are polymerized analogously to Example 11:

| | |
|---|---|
| Vinyl acetate | 80 g |
| Vinylacetic acid | 10 g |
| Polyethylene glycol of MW 20,000 | 10 g |
| Tetraallyloxyethane | 0.2 g |
| Benzoyl peroxide | 3 g |

Characteristics of the polymer obtained:
Acid number: 63
Viscosity: (2% of polymer neutralized with 2-amino-2-methyl-1-propanol, dissolved in 50% strength aqueous ethanol, at 34.6°C): 2.83 cps.

EXAMPLE 17

The following are polymerized analogously to Example 1:

| | |
|---|---|
| Vinyl acetate | 85 g |
| Crotonic acid | 5 g |
| Polyethylene glycol of MW 20,000 | 10 g |
| Tetraallyloxyethane | 0.2 g |
| Benzoyl peroxide | 3 g |
| 0.2% strength solution of Cellosize in water | 200 g |
| Sodium chloride | 76 g |

Characteristics of the polymer obtained:
Acid number: 37
Viscosity (5% strength solution in DMF at 35°C): 2.63 cps

EXAMPLE 18

The following are polymerized analogously to Example 11:

| | |
|---|---|
| Vinyl propionate | 80 g |
| Crotonic acid | 10 g |
| Polyethylene glycol of MW 20,000 | 10 g |
| Tetraallyloxyethane | 0.2 g |
| Benzoyl peroxide | 2 g |

Characteristics of the polymer obtained:
Acid number: 84
Viscosity (2% of polymer neutralized with 2-amino-2-methyl-1-propanol, dissolved in 50% strength aqueous ethanol, at 34.6°C): 3.53 cps.

EXAMPLE 19

The following are polymerized analogously to Example 11:

| | |
|---|---|
| Vinyl acetate | 45 g |
| Diethyl maleate | 35 g |
| Crotonic acid | 10 g |
| Polyethylene glycol of MW 20,000 | 10 g |
| Tetraallyloxyethane | 0.2 g |
| Azo-bis-isobutyronitrile | 1.5 g |

Characteristics of the polymer obtained:
Acid number: 67.3
Viscosity (2% of polymer neutralized with 2-amino-2-methyl-1-propanol, dissolved in 50% strength aqueous ethanol, at 34.6°C): 2.5 cps.

EXAMPLE 20

The following are polymerized analogously to Example 11:

| | |
|---|---|
| Methyl methacrylate | 80 g |
| Acrylic acid | 10 g |
| Polyethylene glycol of MW 20,000 | 10 g |
| Ethylene glycol dimethacrylate | 0.02 g |
| Azo-bis-isobutyronitrile | 1.5 g |

Characteristics of the polymer obtained:
Acid number: 68.6
Viscosity (2% of polymer neutralized with 2-amino-2-methyl-1-propanol, dissolved in 50% strength aqueous ethanol, at 34.6°C): 5.7 cps.

EXAMPLE 21

The following are polymerized analogously to Example 11:

| | |
|---|---|
| Hexene-1 | 30 g |
| N-vinylpyrrolidone | 60 g |
| Polyethylene glycol of MW 20,000 | 10 g |
| Tetraallyloxyethane | 0.1 g |
| Azo-bis-isobutyronitrile | 1.5 g |

Characteristics of the polymer obtained:
Viscosity (2% of polymer neutralized with 2-amino-2-methyl-1-propanol, dissolved in 50% strength aqueous ethanol, at 34.6°C): 3 cps.

EXAMPLE 22

The following are polymerized analogously to Example 11:

| | |
|---|---|
| Vinyl acetate | 70 g |
| Cetyl vinyl ether | 10 g |
| Allyloxyacetic acid | 10 g |
| Polyethylene glycol of MW 20,000 | 10 g |
| Tetraallyloxyethane | 0.01 g |
| Azo-bis-isobutyronitrile | 1.75 g |

Characteristics of the polymer obtained:
Acid number: 47
Viscosity (2% of polymer neutralized with 2-amino-2-methyl-1-propanol, dissolved in 50% strength aqueous ethanol, at 34.6°C): 2.99 cps.

EXAMPLE 23

The following are polymerized analogously to Example 11:

| | |
|---|---|
| Vinyl acetate | 70 g |
| Stearyl vinyl ether | 10 g |
| Crotonic acid | 10 g |
| Polyethylene glycol of MW 20,000 | 10 g |
| Tetraallyloxyethane | 0.01 g |
| Azo-bis-isobutyronitrile | 1.75 g |

Characteristics of the polymer obtained:
Acid number: 65
Viscosity (2% of polymer neutralized with 2-amino-2-methyl-1-propanol, dissolved in 50% strength aqueous ethanol, at 34.6°C): 3.85 cps.

EXAMPLE 24

The following are polymerized analogously to Example 11:

| | |
|---|---|
| Vinyl acetate | 70 g |
| Vinyl laurate | 10 g |
| Crotonic acid | 10 g |
| Polyethylene glycol of MW 20,000 | 10 g |
| Tetraallyloxyethane | 0.02 g |
| Benzoyl peroxide | 2 g |

Characteristics of the polymer obtained:
Acid number: 63
Viscosity (2% of polymer neutralized with 2-amino-2-methyl-1-propanol, dissolved in 50% strength aqueous ethanol, at 34.6°C): 3.7 cps.

EXAMPLE 25

The following are polymerized analogously to Example 11:

| | |
|---|---|
| Vinyl acetate | 70 g |
| Allyl laurate | 5 g |
| Crotonic acid | 10 g |
| Polyethylene glycol of MW 20,000 | 15 g |
| Tetraallyloxyethane | 0.2 g |

-continued

Benzoyl peroxide     3 g

Characteristics of the polymer obtained:
Acid number: 66
Viscosity (2% of polymer neutralized with 2-amino-2-methyl-1-propanol, dissolved in 50% strength aqueous ethanol, at 34.6°C): 3.1 cps.

EXAMPLES OF COMPOSITIONS

EXAMPLE A

A hair lacquer is prepared according to the invention by mixing the following ingredients:

| | |
|---|---|
| Polymer prepared according to Example 4 2-Amino-2-methyl-1,3-propanediol, pH 7 | 8 g |
| Ethyl alcohol, q.s.p. | 100 g |

25 grams of this solution are packaged in an aerosol container with 45 g of liquefied gaseous propellant $F_{11}$ (trichlorofluoromethane) and 30 g of $F_{12}$ (dichlorodifluoromethane).

After spraying this lacquer onto the head of hair, the hair is glossy and keeps its shape excellently.

This lacquer is completely removed by brushing and there is no accumulation of resin on the hair even after several applications.

In this example, the polymer prepared according to Example 4 can advantageously be replaced by the same amount of one of the polymers prepared according to Examples 3, 6, 8, 12 and 18.

EXAMPLE B

A hair lacquer is prepared according to the invention by mixing the following ingredients:

| | |
|---|---|
| Polymer prepared according to Example 7 2-Amino-2-methyl-1-propanol, pH = 8 | 6 g |
| Ethyl alcohol, q.s.p. | 100 g |

25 grams of this solution are packaged in an aerosol container with 45 g of $F_{11}$ and 30 g of $F_{12}$.

An excellent lacquer, which causes the head of hair to keep its shape excellently, is thus obtained.

In this example, the polymer prepared according to Example
amount of one of the polymers prepared according to Examples 5, 9, 10, 22 and 23.

EXAMPLE C

An aerosol hair lacquer is prepared according to the invention by mixing the following ingredients:

| | |
|---|---|
| Polymer prepared according to Example 14 2-Amino-2-methyl-1,3-propanediol, pH = 7 | 8 g |
| Isopropyl alcohol, q.s.p. | 100 g |

25 grams of this solution are packaged in an aerosol container with 45 g of $F_{11}$ and 30 g of $F_{12}$.

An excellent lacquer, which makes the hair glossy but not sticky, is thus obtained. It is also found that the head of hair keeps its shape excellently over a period of time.

EXAMPLE D

An aerosol lacquer is prepared according to the invention by mixing the following ingredients:

| | |
|---|---|
| Polymer prepared according to Example 16 2-Amino-2-methyl-1-propanol, pH = 7.5 | 7 g |
| Ethyl alcohol, q.s.p. | 100 g |

30 grams of this mixture are then packaged in an aerosol container with 40 g of $F_{11}$ and 30 g of $F_{12}$.

In this example, the polymer prepared according to Example 16 can advantageously be replaced by the same amount of the polymer prepared according to Example 19 or Example 2.

EXAMPLE E

A wavesetting lotion is prepared according to the invention by mixing the following ingredients:

| | |
|---|---|
| Polymer prepared according to Example 19 2-Amino-2-methyl-1-propanol, pH = 7 | 2 g |
| Ethyl alcohol | 45 g |
| Water, q.s.p. | 100 g |

When this lotion is applied to hair, it produces a non-sticky film which does not powder and which causes the head of hair to keep its shape excellently.

In this example, the polymer prepared according to Example 19 can advantageously be replaced by the same amount of one of the polymers prepared according to Examples 22 and 23.

EXAMPLE F

A wavesetting lotion is prepared according to the invention by mixing the following ingredients:

| | |
|---|---|
| Polymer prepared according to Example 12 2-Amino-2-methyl-1,3-propanediol, pH = 7 | 1.5 g |
| Isopropyl alcohol | 30 g |
| Water, q.s.p. | 100 g |

In this example the polymer prepared according to Example 12 can advantageously be replaced by the same amount of one of the polymers prepared according to Examples 4, 5, 14, 21 and 25.

EXAMPLE G

A wavesetting lotion is prepared according to the invention by mixing the following ingredients:

| | |
|---|---|
| Polymer prepared according to Example 24 2-Amino-2-methyl-1-propanol, pH = 7.2 | 3.5 g |
| Ethyl alcohol | 40 g |
| Water, q.s.p. | 100 g |

When this lotion is applied in the conventional manner it causes the hair to keep its shape excellently over a period of time.

EXAMPLE H

A wavesetting lotion is prepared according to the invention by mixing the following ingredients:

| | |
|---|---|
| Polymer prepared according to Example 3 | 2 g |
| Perfume | 0.1 g |
| Ethyl alcohol | 45 g |
| Water, q.s.p. | 100 g |

An excellent wavesetting lotion is thus obtained, which enables the hair to keep its shape very well.

In this example, the copolymer prepared according to Example 3 can advantageously be replaced by the same amount of the polymer prepared according to Example 21.

EXAMPLE I

A wavesetting lotion is prepared according to the invention by mixing the following ingredients:

| | |
|---|---|
| Polymer prepared according to Example 2 | 1.5 g |
| 2-Amino-2-methyl-1,3-propanediol, pH = 7 | |
| Isopropyl alcohol | 35 g |
| Perfume | 0.1 g |
| Water, q.s.p. | 100 g |

When this lotion is applied in the conventional manner and the hair is dried on 15 to 30 mm rollers, excellent waves which keep for a long time are produced.

In this example, the polymer prepared according to Example 2 can advantageously be replaced by the same amount of a polymer prepared according to Examples 5, 11, 13 to 15 and 20.

EXAMPLE J

A wavesetting lotion is prepared according to the invention by mixing the following ingredients:

| | |
|---|---|
| Polymer prepared according to Example 6 | 2.2 g |
| 2-Amino-2-methyl-1-propanol, pH = 7.3 | |
| Ethyl alcohol | 60 g |
| Perfume | 0.2 g |
| Water, q.s.p. | 100 g |

This lotion gives excellent wavesetting and the hair is glossy, supple and springy.

It is also found that the locks keep their shape excellently even in a very humid atmosphere.

In this example, the polymer prepared according to Example 6 can advantageously be replaced by the same amount of a polymer prepared according to Examples 7 to 10, 12 and 16 to 19.

I claim:

1. A hair cosmetic composition comprising in a solvent selected from the group consisting of water, an aliphatic alcohol having 1 to 6 carbon atoms and an aqueous-alcoholic solution of said alcohol, 0.4 to 5% by weight of a graft and cross linked copolymer constituted by:
   a. 5 to 85% by weight of at least one monomer selected from the group consisting of: vinyl acetate, vinyl stearate, vinyl laurate, vinyl propionate, allyl stearate, allyl laurate, diethyl maleate, allyl acetate, methyl methacrylate, cetyl vinyl ether, stearyl vinyl ether and hexene-1;
   b. 3 to 80% by weight of a monomer selected from the group consisting of: crotonic acid, allyloxyacetic acid, vinylacetic acid, acrylic acid, methacrylic acid and N-vinylpyrrolidone;
   c. 2 to 50% by weight of polyethylene glycol having a molecular weight between 300 and 30,000; and
   d. 0.01 to 8% by weight, based on the total weight of (a) + (b) + (c) of a cross-linking agent selected from the group consisting of: ethylene glycol dimethacrylate, diallyl O-phthalate, diallyl M-phthalate, diallyl P-phthalate, tetraallyloxyethane, and a polyallylsucrose having 2 to 5 allyl groups per mol of sucrose, said copolymer having a molecular weight between 10,000 and 1,000,000.

2. The composition according to claim 1 in which the copolymer contains free carboxyl groups which have been neutralized with an organic or inorganic base in an amount between 50 and 100% of the stoichiometric amount.

3. The composition according to claim 2 in which the base is selected from the group consisting of ammonia, monoethanolamine, diethanolamine, triethanolamine, an isopropanolamine, morpholine, 2-amino-2-methyl-1-propanol and 2-amino-2-methyl-1,3-propanediol.

4. The composition according to claim 1 in which the aqueous-alcoholic solution contains from 5 to 70% by weight of said aliphatic alcohol.

5. A method of setting hair which comprises applying to the hair an effective amount of the composition of claim 1, winding the hair on wavesetting rollers and drying the hair.

* * * * *